US00RE36844E

United States Patent [19]

Jones et al.

[11] E Patent Number: Re. 36,844

[45] Reissued Date of Patent: Aug. 29, 2000

[54] CELLULAR ATTACHMENT TO TRANS-EPITHELIAL APPLIANCES

[75] Inventors: Jonathan C. R. Jones, Chicago, Ill.; Vito Quaranta, La Jolla, Calif.; Richard Tamura, Kent, Wash.

[73] Assignee: Desmos Incorporated, San Diego, Calif.

[21] Appl. No.: 09/213,632

[22] Filed: Dec. 17, 1998

Related U.S. Patent Documents

Reissue of:

[64] Patent No.: 5,585,267
Issued: Dec. 17, 1996
Appl. No.: 08/317,223
Filed: Oct. 3, 1994

U.S. Applications:

[63] Continuation-in-part of application No. 08/042,727, Apr. 5, 1993, abandoned, application No. 08/151,134, Nov. 12, 1993, Pat. No. 5,422,264, and application No. 08/152,460, Nov. 12, 1993, Pat. No. 5,510,263.

[51] Int. Cl.[7] ..... C12N 5/00; A01N 1/02; A61B 17/00; A61B 17/08

[52] U.S. Cl. ..... 435/240.243; 435/240.2; 435/240.23; 435/283.1; 606/1; 606/151; 606/167

[58] Field of Search ..... 435/240.2, 240.243, 435/240.23, 283.1; 606/1, 151, 167

[56] References Cited

U.S. PATENT DOCUMENTS

| | | | |
|---|---|---|---|
| 4,836,884 | 6/1989 | McAuslan et al. | 156/629 |
| 4,963,490 | 10/1990 | Chuchouse et al. | 435/240.241 |
| 5,007,925 | 4/1991 | Tsilibary et al. | 623/1 |
| 5,256,418 | 10/1993 | Kemp et al. | 424/423 |
| 5,266,476 | 11/1993 | Sussman et al. | 435/240.23 |
| 5,278,063 | 1/1994 | Hubbell et al. | 435/240.241 |
| 5,330,911 | 7/1994 | Hubbell et al. | 435/240.241 |
| 5,352,668 | 10/1994 | Burgeson et al. | 514/21 |
| 5,385,836 | 1/1995 | Kimura et al. | 435/177 |
| 5,415,938 | 5/1995 | Cahalan et al. | 428/409 |
| 5,422,264 | 6/1995 | Quaranta et al. | 435/240.2 |
| 5,453,278 | 9/1995 | Chan et al. | 424/422 |
| 5,510,263 | 4/1996 | Quaranta et al. | 435/240.243 |
| 5,512,474 | 4/1996 | Clapper et al. | 435/240.243 |
| 5,681,587 | 10/1997 | Halberstadt et al. | 424/562 |

FOREIGN PATENT DOCUMENTS

| | | |
|---|---|---|
| WO 92/17498 | 10/1992 | WIPO . |
| WO 94/05316 | 3/1994 | WIPO . |
| WO 94/23016 | 10/1994 | WIPO . |
| WO 95/13103 | 5/1995 | WIPO . |

OTHER PUBLICATIONS

Hormia et al., Journal of Investigative Dermatology, 105(4), "Rapid Spreading and Mature Hemidesmosome Formation in HaCaT Keratinocytes Induced by Incubation with Soluble Laminin–5r", pp. 557–561, Oct. 1995.

Baker et al., Experimental Cell Research, 228(2), "Morphogenetic Effects of Soluble Laminin–5 on Cultured Epithelial Cells and Tissue Explants", pp. 262–270, Nov. 1996.

El–Ghannam et al., J. Biomed. Mater. Res., 41(1), "Laminin–5 Coating Enhances Epithelial Cell Attachment, Spreading, and Hemidesmosome Assembly on Ti–6AI–4V Implant Material in vitro", pp. 30–40, Jul. 1998.

Tamura et al., J. Peridontal Res., 32(3), "Coating of Titanium Alloy with Soluble Laminin–5 Promotes Cell Attachment and Hemidesmosome Assembly in Gingival Epithelial Cells: Potential Application to Dental Implants", pp. 287–294, Apr. 1997.

Boukamp, et al., Normal Keratiniaztion in a Spontaneously Immortalized Aneuploid Human Keratinocyte Cell Line, *J. of Cell Bio.,* 106:761–771 (1988).

Chapman, et al., Abnormal Expression of Hemidesmosome–Like Structures By Junctional Epidermolysis Bullosa Keratinocytes In Vitro, *Brit. J. of Dermatology,* 123:137–144 (1990).

Garrison, et al., Drosphila Laminin A Chain Sequence, Interspecies Comparison, and Domain Structure of a Major Carboxyl Portion, *J. of Biol. Chem,* 266(34):22899–22904 (1991).

Giudice, et al., Identification of Two Collagen Domains Within the Bullous Pemphigoid Autoantigen BP180, *J. Clin. Invest.,* 87:734–738 (1991).

Hieda et al., Identification of a New Hemidesmosomal Protein, HD1: A Major, High Molecular Mass Component of Isolated Hemidesmosomes, *J. of Cell Bio.,* 116(6):1497–1506 (1992).

Hopkinson, et al., Expressions of Hemidesmosomal Plaque Components, *J. Cell Bio.,* 111:(5.Pt.2), 408a (1990).

Hopkinson, et al., Cytoplasmic Domain of the 180–kD Bullous Pemphigoid Antigen, A Hemidesmosomal Component: Molecular and Cell biologic Characterization, *J. of Invest. Dermatology* 99(3):264–270 (1992).

Hormia, et al., The Distribution of Intergring α6β4 In Keratinocytes Is Modulated By Rat Carcinoma Cells, *Meeting of the International Association for Dental Research,* Chicago, IL, (1993) (Abstract).

Izumi, et al., In Vitro Induction of Ornithine Dercarboxylase in Urinary Bladder Carcinoma Cells, *Cancer Research,* 41:405–409 (1981).

(List continued on next page.)

*Primary Examiner*—Jon P. Weber
*Attorney, Agent, or Firm*—Knobbe Martens, Olson & Bear, LLP

[57] ABSTRACT

A trans-epithelial appliance having a hemidesmosome formation-inducing protein composition derived from rat bladder carcinoma cells deposited thereon. This composition stimulates cell attachment and may be either the cell matrix or a soluble factor isolated from the conditioned medium. The appliance will be useful for diminishing inflammation and/or infection at the site of entry of the appliance. The appliance may also be used to stimulate gum junctional epithelium adhesion in the treatment of gingivitis and periodontitis. The composition may be used to maintain tissues ex vivo.

18 Claims, No Drawings

OTHER PUBLICATIONS

Jones et al., Intermediate Filament–Plasma Membrane Interactions, *Cell Bio.,* 3:127–132, (1991).
Jones et al., α6β4 Integrins: Their Role in the assembly of the Hemidsomsome (HD) and in Signal Transduciton, *J. Cellular Biochem.,* 16F:142, (1992).
Kallunki, et al., A Truncated Laminin Chain Homologous to the B2 Chain: Structure, Spatial Expressions, and Chromosomal Assignment, *J. of Cell Bio.,* 119(3):679–693 (1992).
Klatte, et al., Immunochemical Characterization of Three Components of the Hemidesmosome and Their Expression in Cultured Epithelial Cells, *J. of Cell Bio.,* 109(6Pt.2):3377–3390 (1989).
Kurpakaus, et al., Intergrins in the Hemidesmosome, *J. Cell Bio.,* 111:(5.Pt.2), (1990).
Kurpakus, et al, Surface Relocation of Alpha6Beta4 Intergrins and Assembly of Hemidesmosomes in an In Vitro Model of Wound Healing, *J. of Cell Bio.,* 115(6):1737–1750 (1991).
Langhofer, et al., Matrix Signals Transduced by the α6β4 Integrin Complex, *Mol. Biol. Cell,* 3(Suppl.):95a (1992).
Langhofer, et al., The Matrix Secreted By 804G Cells Contains Laminin–Related Components that Participate in Hemidesmosome Assembly In Vitro, *J. of Cell Science,* 105:753–764 (1993).
Riddelle, et al., Characterization of a Novel Cut–Substratum Attachment Device in Cultured Epithelial Cells, *J. Cell Biol.,* 109(4Pt.2):201a (1989).
Riddelle, et al., Hemidesmosomes in Cultured Cells, *J. Cell Biol.,* 111(5Pt.2):2270 #408a.
Riddelle, et al., Formation of Hemidesmosomes In Vitro by A Transformed Rat Bladder Cell Line, *J. of Cell Bio.,* 112(1):159–168 (1991).
Riddelle, et al., Dynamic Aspects of Hemidesmosomes in the Novel Epithelial Cell Line 804G, *J. of Cell Bio.,* 115(3Pt2):41a (1991).
Riddelle, et al, Hemidesmosomes in the Epithelial Cell Line 804G: Their Fate During Wound Closure, Mitosis and Drug Induced Reorganization of the Cytoskeleton, *J. Cell Science,* 103:475–490 (1992).
Riddelle, et al., Substrate Attachment is Necessary for the Expression of Hemidesmosomal Proteins in Cultured Cells, *Mol. Biol. Cell,* 3(Suppl.):70a (1992).

Rousselle, et al., Kalinin: An Epithelium–Specific Basement Membrane Adhesion Molecule that is a Component of Anchoring Filaments, *J. of Cell. Bio.,* 114(3):567–576 (1991).

Rousselle, et al., Kalinin is More Efficent Than Laminin in Promoting Adhesion of Primary Keratinocytes and Some Other Epithelial Cells and Has A Difference Requirement for Integrin Receptors, *J. of Cell. Bio.* 125(1):205–214 (1994).

Schwarz, et al., Desmosomes and Hemidesmosomes Constitutive Molecular Components, *Annu. Rev. Cell Biol.,* 6:461–491 (1990).

Sonnenberg, et al., integrin α6β4 Complex is Located in Hemidesmosomes, Suggesting a Major Role in Epidermal Cell–Basement Membrane Adhesion, *J. of Cell Bio.,* 113(4):907–917 (1991).

Staehelin, Structure and Function of Intracellular Junctions, *Dept. of Mol. Cellular and Developmental Biology,* Univ. of Colorado, Boulder, CO, 191–283.

Stepp et al., α6β4 Integrin Heterodimer is a Component of Hemidesmosomes, *Proc. Natl. Acad. Sci. USA,* 87:8970–8974 (1990).

Budavari, et al., (eds.), The Merck Index, 11$^{th}$ ed., *Merck & Co., Inc.,* Rahway, N.J., p. 544 (1989).

Jones, et al., A Function For The Integrin α6β4 in the Hemidesmosome, *Cell Regulation* 2:427–438 (1991).

Riddelle, Dissertation Abstracts International, 55(1):22B–23B (1994).

Langhofer, Dissertation Abstracts International, 56(3):1199B–1200B (1995).

Hopkinson, et al., Molecular Biology of the Cell, 4(suppl.), abstract #568, p. 97a (1993).

CELLULAR ATTACHMENT TO TRANS-EPITHELIAL APPLIANCES

Matter enclosed in heavy brackets [ ] appears in the original patent but forms no part of this reissue specification; matter printed in italics indicates the additions made by reissue.

CROSS-REFERENCE TO RELATED APPLICATIONS

This application *is a Reissue of 08/317,223, filed Oct. 3, 1994, now U.S. Pat. No. 5,585,267, which* is a continuation-in-part of U.S. application Ser. No 08/042,727, filed Apr. 5, 1993 (abandoned) and U.S. application Ser. Nos. 08/151,134 (U.S. Pat. No. 5,422,264) and 08/152,460 (U.S. Pat No. 5,510,263) both filed Nov. 12, 1993.

FIELD OF THE INVENTION

The present invention relates to the attachment of cells to shaped articles. More specifically, the invention relates to the attachment of epithelial cells to biologically compatible implants and appliances.

BACKGROUND OF THE INVENTION

When organs of the body are formed, they develop in neatly organized arrays. Often, cell types are separated by connective tissue called basement membranes. In skin, for instance, the superficial layer of epidermal cells adheres to the underlying basement membrane. This skin basement membrane acts as a barrier between the epidermal cells on the outside, and the dermal cells underneath. A similar arrangement of cells occurs in the lining of the gut and in the oral cavity.

Basement membranes have been implicated in the growth, attachment, migration, repair and differentiation of their overlying cell populations. Three layers have been defined in basement membranes: a) the lamina lucida, an electronmicroscopically clear region in close approximation to the overlying cells; b) the lamina densa, an electron dense region of 20–300 nm in width; and c) the sublamina densa which contains anchoring fibrils, microfibrillar bundles and collagen fibers.

Many epithelial cells interact with the underlying extracellular matrix, a network of proteins to which cells attach, via a junction called the hemidesmosome (Staehelin, (1974) Structure and Function of Intercellular Junctions, Department of Molecular, Cellular and Developmental Biology, University of Colorado, Boulder, Colo., 191–283). The hemidesmosome, with its anchored structures including intermediatei filaments and anchoring fibrils, forms an adhesion complex. The purification of adhesion-facilitating proteins has remained elusive. Burgeson et al (PCT Applications No. WO92/17498 and WO94/05316) disclose a protein, kalinin, which is said to facilitate cell adhesion to substrates; however, this material is apparently inactive with respect to hemidesmosome formation.

When cultured on tissue culture plastic in vitro, most epithelial cells do not assemble bona fide hemidesmosomes despite the fact that they appear to express all of the necessary plaque and hemidesmosomal components. The 804G and NBT-II rat bladder carcinoma cell lines were recently discovered to have the ability to readily assemble hemidesmosomes in vitro under standard culture conditions (Riddelle et al., (1991) J. Cell Biol., 112:159–168; Hieda et al., (1992), J. Cell Biol., 116:1497). It has also been reported that substratum-induced staining by anti-hemidesmosome antibodies is greatly diminished in 804G cell cultures that enter in vitro wound sites (Riddelle et al., (1992) J. Cell Sci., 103:475–490).

As described in Langhofer et al. (1993) J. Cell Sci., 105:753–764) and in copending U.S. application Ser. No. 08/042,727, hereby incorporated by reference, when epithelial cells unable to themselves form hemidesmosomes are plated on the cell matrix secreted by 804G cells, hemidesmosome formation is induced. In addition, copending U.S. application Ser. No. 08/151,134, hereby incorporated by reference, teaches that a soluble factor produced by 804G cells can also induce attachment and hemidesmosome formation in cells contacted with the factor. Further, this pending application discloses that the 804G factor is comprised of protein components having significant similarity to human merosin, a lantinin A isoform, and to Drosophila lantinin A. Copending U.S. application Ser. No. 08/152,460, also incorporated by reference, discloses the enhanced growth of pancreatic endocrine precursor cells plated on the 804G matrix.

Any medical device, including indwelling catheters and colostomy tubes, which breach the skin for an extended period of time will result in inflammation and/or infection. It would be particularly desirable to coat the surface of these devices with epithelial cells prior to or after insertion into the skin to prevent these undesirable processes. It would also be desirable to coat surgical meshes with epithelial cells for use in skin allografts. In addition, periodontitis, a severe form of gum disease resulting in destruction of gum tissue epithelium and bone erosion, would be amenable to treatment with dental abutment pieces coated with epithelial cells. This would promote reattachment of detached gum tissue to the tooth surface.

The maintenance of tissues and organs ex vivo is also highly desirable. Tissue replacement therapy is well established in the treatment of human disease. For example, around 42,000 corneal transplants were performed in the United States in 1993. Human epidermal cells can already be grown in vitro and used to populate bum sites and chronic skin ulcers. However, many primary cells and tissues are difficult to establish in vitro on normal tissue culture plastic. Although this problem is partially alleviated by the use of extracellular matrix-coated cell supports, this is only a temporary solution.

Thus, there is a need for trans-epithelial appliances capable of stimulating epithelial cell attachment and spreading and for a composition capable of supporting the viability of tissues and organs maintained ex vivo. The present invention satisfies these needs.

SUMMARY OF THE INVENTION

One embodiment of the present invention is an article of manufacture, comprising:

a trans-epithelial appliance; and a hemidesmosome formation-inducing composition deposited on the appliance, wherein the composition is hemidesmosome-inducing 804G matrix protein.

Preferably, the article is a shaped article which is either an indwelling catheter, needle, metal pin, metal rod, colostomy tube, dental abutment piece or surgical mesh. The composition may be either a cell matrix deposited by or soluble factor secreted by 804G cells. In another aspect of this preferred embodiment, the appliance is used in vivo. Advantageously, the appliance is made of or coated with a biocompatible metal which may be either stainless steel or titanium. Alternatively, the appliance is made of or coated with a ceramic material. This material is preferably hydroxyapatite. According to another aspect of this preferred embodiment, the appliance is made of or coated with a polymer. Advantageously, the polymer is polyester, polyglycolic acid or a polygalactose-polyglycolic acid copolymer.

The present invention also provides a method for inducing epithelial cell attachment to a trans-epithelial appliance, comprising coating the appliance with a hemidesmosome formation-inducing composition prior to incubation with epithelial cells, wherein the composition is hemidesmosome-inducing 804G matrix protein. The composition may advantageously be a cell matrix deposited by or a soluble lo factor secreted by 804G cells. According to another aspect of this embodiment, the appliance is either an indwelling catheter, needle, metal pin, metal rod, colostomy tube, dental abutment piece or surgical mesh. Preferably, the appliance is made of or coated with a polymer. The polymer may be polyester, polyglycolic acid or a polygalactose-polyglycolic acid copolymer.

Another embodiment of the invention is a method for preserving corneal explants ex vivo, comprising culturing the explants in a medium containing a hemidesmosome-inducing soluble protein factor, wherein the factor is the hemidesmosome-inducing soluble factor secreted by 804G rat bladder carcinoma cells. Preferably, the medium is 804G conditioned medium.

Still another embodiment of the invention is a method for inducing epithelial cell attachment to a surface, comprising applying a hemidesmosome-inducing composition to the surface, wherein the composition is hemidesmosome-inducing 804G matrix protein. Advantageously, the composition is either a cell matrix deposited by or soluble factor secreted by 804G cells.

DETAILED DESCRIPTION OF THE INVENTION

The present invention provides trans-epithelial appliances coated with a hemidesmosome-inducing factor which stimulates epithelial cell attachment, spreading and hemidesmosome formation. The enhanced attachment, spreading and hemidesmosome formation of epithelial cells plated on the 804G matrix or contacted with the soluble factor secreted by 804G cells will have significant applications in the promotion of cell adhesion in vivo. The 804G factors will enhance attachment and spreading of epithelial cells subsequently plated on the coated appliance.

The 804G cell line is described by Izumi et al., Cancer Res., (1981) 41:405–409, and was deposited under the Budapest Treaty with the American Type Culture Collection, Rockville, Md., on Feb. 24, 1994, and assigned accession number ATCC CRL 11555. The NBT-II cell line was also deposited on Feb. 24, 1994, and assigned accession number ATCC CRL 11556.

The present invention provides matrix proteins, produced by such cells as 804G cells and NBT-II cells, that can stimulate cell attachment, spreading and modulate the organization of hemidesmosomal components in unrelated cells plated on the matrix-coated trans-epithelial appliance. The term "trans-epithelial" appliance indicates any shaped article which penetrates the epithelium. Such appliances include, but are not limited to, dental abutment pieces, needles, metal pins or rods, indwelling catheters, colostomy tubes and surgical meshes made of biocompatible materials. The individual protein components of the matrix may also be isolated and used to coat the appliance. Alternatively, the conditioned medium from 804G cells or the purified soluble protein factors can be isolated from the conditioned medium and used to coat the appliances. Moreover, components of the 804G matrix or soluble factor may be recombinantly produced and used as an appliance coating. The coating of any desired surface capable of supporting cell adhesion with the 804G matrix, matrix components, 804G conditioned medium, conditioned medium components or recombinantly-produced matrix components is within the scope of the present invention.

Although methods related to production and isolation of the 804G cell matrix and soluble factor are specifically disclosed, it will be appreciated that any cell matrix having the ability to support cell adhesion, spreading and hemidesmosome formation is within the scope of the present invention. It should be noted that the term "804G matrix" is used to generically refer to any cell matrix with the ability to stimulate cell attachment and hemidesmosome formation.

One major use contemplated for the active components of the 804G matrix and soluble factor is in cell growth and attachment. A substrate upon which cells are to be grown is coated with the soluble factor, 804G matrix, or purified or recombinant hemidesmosome-inducing components thereof. The epithelial cells to be grown are then plated on or applied to the desired substrate, and grown on the matrix under normal epithelial cell culture conditions. Such cells, including human cells in vivo and in vitro, will grow in an organized, tissue-like fashion on the substrate and will attach and form hemidesmosomes. Hemidesmosome formation promoted by the matrix and soluble factor is a major advantage, because it greatly enhances cell attachment. It also appears that the organization of cells grown on the matrix or soluble factor is significantly more advanced and tissue-like than control cells.

The substrate used herein may be any desired substrate. For laboratory use, the substrate may be as simple as glass or plastic. For use in vivo, the substrate may be any biologically compatible material capable of supporting cell growth. Suitable substrate materials include shaped articles made of or coated with such materials as collagen, regenerated collagen, polyglycolic acid, polygalactose, polylactic acid or derivatives thereof; biocompatible metals such as titanium and stainless steel; ceramic materials including prosthetic material such as hydroxylapatite; synthetic polymers including polyesters and nylons; polystyrene; polyacrylates; polytetrafluoroethylene and virtually any other material to which biological molecules can readily adhere. The determination of the ability of a particular material to support adhesion of the 804G matrix or soluble factor will require only routine experimentation by the skilled artisan.

One particular use of the present invention is to increase epithelial cell adhesion to target surfaces. For example, prostheses for dental implantation may be coated with the 804G matrix or soluble factor to stimulate periodontal cell attachment. These prostheses typically comprise two separate pieces, an implant which is inserted into the bone and an abutment piece which actually contacts the junctional epithelium. Alternatively, the implant and abutment piece may be obtained as a single unit. In a preferred embodiment, the implants and abutment pieces are both made of titanium. Existing teeth may also be similarly coated with the matrix or soluble factor as a treatment for gum (junctional epithelium) disease, namely gingivitis and periodontitis, which promote the detachment of the gum from the tooth. These disease conditions allow the accumulation of food and other foreign matter in the space between the gum and the tooth, resulting in infection. The 804G matrix and soluble factor will promote reattachment of the gum to the tooth, thus preventing entry of foreign matter and subsequent infection.

If the substrate is made of a natural or synthetic bioerodible material in the form of a mesh, sheet or fabric, the matrix materials or soluble factor may be applied directly to the surface thereof (see Examples 8 and 9) or mixed in with the composition. Epithelial cells may then be cultured on the matrix to form transplantable or implantable appliances, including dental abutment pieces, needles, metal pins or rods, indwelling catheters, colostomy tubes, surgical meshes and any other appliance for which coating with the matrix or soluble factor is desirable. Alternatively, the materials may be implanted and cells may be permitted to attach in vivo. The epithelial cell-coated surgical meshes will be useful for skin allografts necessitated by compromised skin integrity.

The appliances of the present invention may coated with the complete, active matrix from 804G cells or a functionally equivalent matrix from other cells, and may also be coated with any one of the individual protein components of the matrix which promotes cell attachment and hemidesmosome formation. The ability of a particular protein component to support these processes will require only routine experimentation by the skilled artisan. Alternatively, the appliance may be coated with the conditioned medium from 804G cells grown in 10% fetal calf serum (FCS) or under low serum conditions (about 1% FCS). Additionally, the appliances may be coated with the soluble factor which has been purified from the cells described hereinabove.

The appliances may be coated by directly culturing 804G cells thereon and then removing the cells, such that the deposited matrix will remain on the appliance. Alternatively, the 804G cells may be cultured in the laboratory on a conventional plastic or glass substrate, removed, and the deposited matrix obtained by scraping, abrading or treatment with low concentrations (about 1%) of sodium dodecyl sulfate (SDS) or other appropriate detergent.

The recovered matrix is then applied to the appliance. The appliance may be immersed in, incubated in, or sprayed with the conditioned medium from 804G cells grown under low or normal serum conditions. The growth of 804G cells under low serum conditions facilitates the purification of the factor from the medium as described in Example 6 hereinbelow. The purified or recombinantly produced soluble factor may also be applied to the appliance in the same manner as described hereinabove. In a preferred embodiment, the concentration of the factor used for coating the appliance is between about 20 $\mu$g/l and about 200 $\mu$g/l. In a particularly preferred embodiment, the concentration is between about 50 $\mu$g/l and about 150 $\mu$g/l.

The conditioned medium may also be used to support tissue and organ growth ex vivo. In human tissue explant culture, 804G matrix is utilized by cells and is incorporated into preexisting basement membranes. For example, in human corneal rims, the soluble laminin variant-containing 804G cell conditioned medium has been used for maintenance of epithelial cell attachment in corneas (Example 10) and induction of assembly of an essential epithelial cell-matrix attachment device in the same tissue.

The corneas may be placed directly in conditioned medium from 804G cells or may be placed in conventional medium supplemented with 804G conditioned medium. The amount of 804G conditioned medium required for optimal corneal maintenance ex vivo will vary depending on the confluency, passage number and particular growth conditions of the cell, although the use of between 10% and 100% conditioned medium (the remainder being normal medium) is contemplated. Optimization of the amount of conditioned medium to use may be determined by one of ordinary skill in the art using routine experimentation. The maintenance of other tissues and organs ex vivo in 804G conditioned medium and 804G conditioned medium-supplemented normal medium is also within the scope of the invention.

Pharmaceutical preparations of the matrix, its active components, or the soluble factor can be prepared in any suitable form, and generally comprise the active ingredient in combination with any of the well known pharmaceutically acceptable carriers. The carriers can be injectable carriers, topical carriers, transdermal carriers, and the like. The preparation may advantageously be in a form for topical administration, such as an ointment, gel, cream, spray, dispersion, suspension or paste. The preparations may further advantageously include preservatives, antibacterials, antifungals, antioxidants, osmotic agents, and similar materials in composition and quantity as is conventional. For assistance in formulating the compositions of the present invention, one may refer to Remington's Pharmaceutical Sciences, 15th Ed., Mack Publishing Co., Easton, Pa. (1975).

The 804G matrix is prepared as described in the following example.

EXAMPLE 1

Preparation of 804G Matrix 804G rat bladder carcinoma cells were maintained at 37° C. in Modified Eagle's Medium with Earle's salts supplemented with 50 U/ml penicillin, 50 $\mu$g/ml streptomycin and 10% FCS (Gibco, Grand Island, N.Y.). The cells were grown to confluency on either plastic Petri dishes or glass coverslips. The culture medium was discarded and the cells were washed in sterile Phosphate Buffered Saline (PBS). The cells were separated from the deposited matrix by incubation for 5 min. in 20 mM $NH_4OH$, followed by three rapid washes with distilled water.

The remaining matrix was removed from the substrate by solubilization in 8M urea, 1% SDS in 10 mMTris-HCl, pH 6.8. The 804G matrix polypeptide profile was analyzed by SDS-polyacrylamide gel electrophoresis (SDS-PAGE) using routine experimental methods known to those of skill in the art. Three major proteins were present in the matrix, ranging in size from 135–150 kD. A minor peptide of 85 kD was also present in the matrix preparation.

EXAMPLE 2

Production of Polyclonal Antibodies against the 804G Matrix

Antiserum was prepared by injecting urea/SDS solubilized cell matrix, as described in Example 1, into a rabbit by standard methods. Briefly, solubilized 804G matrix was mixed with Freund's adjuvant and injected into a rabbit. Serum was collected at three weekly intervals following one booster injection. The isolated polyclonal antiserum (J18) had antibodies recognizing four glycosylated 135–400 kD species as well as the 85 kD polypeptide.

Monoclonal antibodies against the 804G matrix were then produced as described below.

EXAMPLE 3

Production of Monoclonal Antibodies against the 804G Matrix

A mouse monoclonal IgG (5C5) against the 804G cell matrix was prepared by injecting a solubilized 804G cell matrix sample into several mice. At two and three weeks after the initial injection the mice were boosted with further 804G matrix injections. Five days following the final boost, their spleens were removed and isolated spleen cells were fused with the myeloma cell line Sp2 for the production of hybridomas using standard techniques (Galfre and Milsrein, 1981). Hybridoma cells producing antibodies against matrix elements were selected on the basis of their immunoblotting and immunofluorescence reactivities against matrix samples. Selected hybridoma cells were cloned twice by limited-dilution. The 5C5 antibody recognized only a 150 and 140 kD polypeptide in the matrix preparation. Epithelial cells were plated on the matrix and functionally assessed for attachment and hemidesmosome formation as described in the following example.

EXAMPLE 4

Induction of Hemidesmosome Formation by 804G Matrix

Antibodies against a 230 kD plaque component of the hemidesmosome have been detailed previously (Klatte et al., (1989) J. Cell Biol., 109:3377–3390). Monoclonal and polyclonal antibodies directed against the cytoplasmic domain of a 180 kD type II membrane element of the hemidesmosome have been described in Hopkinson et al., (1992) J. Invest. Dermatol., 99:264–270 and Riddelle et al., (1992) J. Cell Sci., 103:475–490) . An antibody against the $\beta_4$ integrin subunit was purchased from Telios Pharmaceuticals (San Diego, Calif.).

Human epidermal carcinoma (SCC12) cells were maintained on the 804G cell matrix for 24 hours to assess the impact of the matrix on hemidesmosome protein localization in a tumor cell line that, under normal circumstances, does not assemble bona fide hemidesmosomes in vitro. Each experiment was repeated at least four times, involving the analysis of more than 500 cells. As controls, SCC12 cells were plated onto other matrices, such as glass and rat tail collagen. After 24 hours, the cells were processed for indirect immunofluorescence using antibodies directed against the 230 kDa, 180 kDa and $\alpha_6\beta_4$ integrin components of the hemidesmosome, double labelled with antibodies against the 804G cell matrix.

Cells on coverslips were first incubated in a mixture of primary antibodies for one hour at 37° C. The coverslips were extensively washed in PBS and then overlaid with the appropriate mixture of rhodamine and fluorescein conjugated secondary antibodies. Processed tissues were viewed on a Zeiss Photomicroscope III fitted with epifluorescence optics. As controls, cells were incubated with normal mouse, rat or rabbit IgG as well as secondary antibodies alone to assess background staining.

In SCC12 cells maintained for 24 hours on glass and rat tail collagen, the 230 kD, 180 kD and $\alpha_6\beta_4$ integrin localized to the periphery of the cells along their substratum attached surfaces. The staining sometimes resembled a fuzzy band surrounding the cell periphery, or linear streaks near the cell edges. Anti-matrix antibodies in the J18 serum generated a diffuse staining along the region of cell-substrate interaction in cells maintained on rat tail collagen, with no obvious correlation to the staining generated by the hemidesmosomal antibody probes. The reactivity of the J18 antibodies with the SCC12 cells by immunofluorescence is consistent with the positive immunoblotting reactivity of J18 antibodies selected from the J18 serum by the human laminin B2t fusion proteins. Since antibodies in the J18 serum failed to recognize rat tail collagen alone, our results provide some indication concerning the matrix that the SCC12 cells themselves secrete.

In SCC12 cells maintained on the 804G cell matrix, the 230 kD, 180 kD and $\alpha_6\beta_4$ integrins show a dramatically different pattern of distribution compared with that observed in cells maintained on rat tail collagen or glass. The patterns that these hemidesmosomal antibodies generate are similar to those seen in 804G cells processed for immunofluorescence using the same antibodies, as described above. Moreover, this staining, in most instances, appears coincident with those patterns generated by antibodies in the whole J18 serum.

In addition, 5C5 antibodies or those J18 antibodies epitope selected from the laminin B2t fusion proteins were also localized in SCC12 cells maintained on the 804G matrix. The distribution of these antibodies compared with that of the 230 kD hemidesmosomal plaque component. It should be noted that the 230 kD antigen distribution in the SCC12 cells mirrors that of the staining generated by the 5C5 and epitope selected antibodies.

Immunoblotting analyses were undertaken to examine whether there was a change in the amounts of both the 230 kD and 180 kD hemidesmosomal components in SCC12 cells maintained on 804G cell matrix for 24 hours compared to SCC12 cells maintained for the same length of time on other matrices. There was no apparent difference in the quantity of both the 230 kD and 180 kD polypeptides in SCC12 cells maintained on the various matrices as assessed by this procedure.

In contrast to hemidesmosomal components, the $\alpha_5\beta_1$ integrin complex, a component of the microfilament-associated adhesion plaque (Burridge et al., 1988), localized primarily at the peripheral cell substratum-associated surface of SCC12 cells regardless of whether it was maintained on rat tail collagen or the 804G cell matrix.

Our studies of epithelial cell growth on the 804G matrix were not confined to SCC12 cells. Normal human keratinocytes (derived from human foreskins), HaCaT (immortalized cells), and SCC13 cells also exhibited almost identical responses when grown on the 804G matrix in comparison to the SCC12 cells discussed above. In each of these cell types, growth on the 804G matrix led to a redistribution of integrins and mature hemidesmosome formation.

In addition, experiments similar to those described above have been performed on the matrix produced by the NBT-II cell line. The results from these experiments are virtually identical to those illustrated for the 804G matrix. Cells grown on NBT-II matrix were stimulated to form mature hemidesmosomes and redistribute intracellular integrins.

Clones corresponding to matrix polypeptides were isolated as described below.

EXAMPLE 5

Isolation of Clones Corresponding to Matrix Polypeptides

A human keratinocyte lambda gtll expression library (Clontech, Inc., Palo Alto, Calif.) was screened with an 804G matrix polyclonal antiserum according to Huynh et al., (DNA Cloning: A Practical Approach, Volume I, D. Glover, Ed., IRL Press, Oxford, 1985). Antibodies absorbed by the fusion protein products of the two clones showed reactivity with the 140 kD and 100 kD molecular weight species in an 804G matrix preparation and a whole cell extract of SCC12 cells. The antiserum was also used to screen a rat 804G expression library. Two independent clones from which antibodies to the 140 kD/100 kD polypeptide components were epitope-selected revealed over 85% identity with stretches of 94 residues in domain IV and 86 residues in domain I/II of a recently identified variant of the B2 chain of laminin that has been termed lantinin B2t (Kallunki et al., (1992) J. Cell Biol., 119:679–685). The B2t variant is not contained in EHS laminin, and therefore represents a new subunit. In addition, five clones from which antibodies to the rat 150 kD component were epitope-selected were isolated.

To further characterize positive clones, plaque lifts of nitrocellulose-bound fusion proteins were used to epitope select antibodies (Sambrook et al., (1989) Molecular Cloning: A Laboratory Manual, 2nd ed., Cold Spring Harbor laboratory Press, Cold Spring Harbor, N.Y.). cDNA inserts were subcloned into M13 vectors and sequenced by the dideoxy chain termination method (Sanger et al., (1977) Proc. Natl. Acad. Sci. U.S.A., 74:5463–5467). Sequence analyses were performed using the GCG sequence analysis software package (University of Wisconsin Biotechnology Center, Madison, Wis.).

The nucleotide sequence of the 140 kDa clone revealed that it encoded a region spanning amino acids 550–810 in domain I/II of human laminin B2t. This experiment illustrates the cross-reactivity of the matrix associated polypeptides with the laminin B2t variant. The 150 kD clones encoded regions exhibiting sequence similarity to the Drosophila laminin A chain (Garrison et al., (1991) J. Biol. Chem., 266:22899–22904). The overall sequence identity between 294 amino acids of the rat 150 kD sequence (SEQ ID NO: 1) and amino acid residues 2365–2724 of the Drosophila laminin A chain (SEQ ID NO: 2) was 25%, a significant overlap considering the evolutionary difference between rat and Drosophila SEQ ID NO: 1 also exhibited 21% identity to amino acids 1634–1970 of human merosin (SEQ ID NO: 3), a laminin A isoform.

The cDNA sequences encoding the protein components of the soluble factor may be inserted into either conventional prokaryotic or eukaryotic expression vectors, widely available from many commercial sources including Stratagene (La Jolla, Calif.), Invitrogen (San Diego, Calif.) and Promega (Madison, Wis.) using routine techniques, transfected into cells, and the expressed protein purified according to well known methods.

804G cells were also found to secrete a soluble factor into the culture medium which was capable of supporting cell attachment and hemidesmosome formation as described below.

EXAMPLE 6

Soluble Factor Treatment of HaCaT Cells

The immortalized human keratinocyte cell line HaCaT, provided by Dr. Norbert Fusenig, Heidelberg, Germany (Boukamp et al., J. Cell Biol., 106:761–771, (1988)), was cultured in DMEM (Bio-Whittaker, Walkersville, Md.) supplemented with 10% FCS and antibiotics. The HaCaT cell line has characteristics very similar to primary keratinocytes. 804G cells and the human embryonic fibroblast cell line WI-38 (ATCC CCL 75) were also cultured under the same conditions.

Fifteen ml culture supernatant was collected from a 75 $cm^2$ culture flask of 804G cells which were approximately 70% confluent, having reached this confluence over 48 hours. Supernatants of HaCaT and WI-38 cells were also collected. HaCaT cells plated on tissue culture plastic in standard medium attach, spread very slowly and still appear rounded 2 hours after seeding. In contrast, when HaCaT cells were seeded in the culture supernatant of 804G cells they attached to the growth substratum and acquired a flattened morphology within 30 minutes. After 24 hours, cells in normal medium formed epithelioid islands, whereas cells seeded in supernatant from 804G cells exhibited a spread-out morphology and appeared to migrate so as to uniformly cover the growth substratum. The 804G culture supernatant effect was evident even if the cells were plated in a 1:1 dilution of the supernatant with normal medium. As a control, HaCaT cells were also plated in their own culture supernatant and in medium collected from cultures of human fibroblasts (WI-38). HaCaT cells plated in either their own medium or WI-38 medium did not exhibit the growth and morphology of those cells plated in 804G medium.

804G cells may also be grown under low serum conditions to facilitate the purification of secreted proteins as described in the following example.

EXAMPLE 7

Growth of 804G Cells under Low Serum Conditions 804G cells were gradually adapted to grow in 1:1 DMEM:OPTI-MEM (Gibco, Grand Island, N.Y.) supplemented with 1% FCS, 2 mM glutamine, 100 $\mu$g/ml penicillin and 50 $\mu$g/ml streptomycin. According to the manufacturer, OPTI-MEM contains low amounts of transferrin and insulin, molecular weights 80 and 6 kDa, respectively, but no other proteins.

The virtual absence of serum proteins in the culture medium simplifies the purification of the hemidesmosome-inducing soluble factors as described below.

EXAMPLE 8

Purification of Soluble Factors from 804G Culture Medium

For the collection of serum-free culture supernatant, confluent 804G cells grown under low serum conditions were removed by trypsinization (0.02%), washed once with DMEM containing 10% FCS and cultured in DMEM:OPTI-MEM without added FCS at a split ratio of 1:6. Culture supernatant was collected when 804G cells had been confluent for 24 hours. The supernatant was centrifuged at 5,000×g for 10 min and stored at −20° C. prior to use. Secreted proteins were purified by precipitation with ammonium sulfate at 40% saturation. Culture supernatant (1 liter) was cleared of particulate material by centrifugation at 10,000×g for 30 min and transferred to another container on ice. Ammonium sulfate was slowly added, with stirring, to 30% saturation. The supernatant was then left at 4° C. overnight to allow complete precipitation. The sample was centrifuged for 30 min at 10,000×g and ammonium sulfate added to a final concentration of 40% saturation. After precipitation and centrifugation, the supernatant was discarded and the pellet resuspended in 1 ml PBS. The protein was dialyzed against PBS, the protein concentration estimated by absorbance at 280 nm. and an aliquot analyzed by SDS-PAGE. Bands of 240, 150 and 140 kDa were observed.

EXAMPLE 9

Adhesion of Epithelial Cells to Soluble Factor-Coated Dental Implants

The three types of titanium implants used were: IMZ titanium plasma sprayed (Interpore International, Irvine, Calif.), HA-coated titanium implant (Calcitek, Carlsbad, Calif.), and a screw-vent titanium implant (Dentsply, Inc., Encino, Calif.). The implant from Interpore had a polished titanium collar that was not covered with the sprayed titanium and the Calcitek implant came with a polished titanium healing screw.

The implants were thoroughly cleaned with a detergent solution, extensively rinsed with tap water followed by deionized water and allowed to dry. Implants were sterilized by immersion in 95% ethanol, rinsed in sterile PBS lacking calcium and magnesium (Bio Whittaker, Walkersville, Md.) and air-dried in a sterile petri dish.

One sample of each type of implant was left untreated, one was coated with 804G culture medium (DMEMC= DMEM containing 10% fetal bovine serum, 2 mM glutamine, 100 units/ml penicillin and 100 $\mu$g/ml streptomycin), and one was coated with 804G conditioned medium collected after four days of cell growth. Coating was performed by placing the implants into sterile 0.65 ml tubes containing DMEMC, 100 $\mu$l 804G conditioned medium, or nothing (untreated control). The implants were placed into the solutions upside down to ensure coating of the exposed polished titanium on the Interpore and Calcitek implants. The samples were then placed at 4° C. overnight (about 16 hours). The implants were removed form the coating solutions and placed into six well tissue culture plates, one implant per well. Nonspecific binding sites on each implant were blocked with 5 ml of 1% (w/v) bovine serum albumin (BSA) in PBS for 5 hours at room temperature. The blocking solution was removed and the implants were washed three times with PBS.

FGmet2 human pancreatic carcinoma cells, an epithelial cell line, were used to test for rapid cell adhesion to the coated implants. The cells were trypsinized and centrifuged at 1500 rpm for 5 minutes. The cell pellet was washed twice by resuspension in 1% BSA in DMEM and centrifuged. The cell pellet was resuspended in 1% BSA in DMEM to a final concentration of $2.2\times10^6$ cells/ml. The six well plates were tilted to allow the implants to rest against one edge of the well and the implants were overlayed with 1 ml of the cell suspension. The cells were incubated with the implants for 30 min at 37° C., removed by aspiration, and the implants washed three times with PBS. The cells were fixed for 5 minutes with 3% paraformaldehyde in 2% sucrose and PBS, and stained for 15 minutes with 0.5% crystal violet in 20% methanol. The excess dye was removed by rinsing under tap water and the implants were examined using an inverted phase microscope.

Significant FGmet2 cell attachment and spreading was observed only on the implants coated with the 804G conditioned medium. This result indicates that hemidesmosome formation-inducing factors secreted by 804G cells can induce epithelial cell attachment and spreading on a shaped, trans-epithelial appliance.

The ability of 804G matrix to coat absorbable and non-absorbable surgical meshes and the subsequent ability of the matrix to support rapid adhesion and cell proliferation was assessed as described in the following two examples.

EXAMPLE 10

Rapid Adhesion of Epithelial Cells to a Surgical Mesh 804G conditioned medium was used as a source of soluble matrix protein. A small piece of polypropylene (PROLENE™), polyester (MERSILENE™), and polyglactin (Vicryl™, a biodegradable copolymer comprising 90% glycolide, a polyglycolic acid derivative and 10% glactide, a polygalactose derivative) mesh (all from Ethicon, Inc.) were each placed into wells of a 24 well tissue culture plate containing either 1 ml 804G conditioned medium or 1 ml DMEM complete medium and incubated overnight at 4° C. The meshes were washed twice with PBS containing 1% BSA (PBS+BSA) and nonspecific binding sites were blocked with PBS+BSA for one hour at room temperature. $4\times10^5$ FGmet2 cells in 1 ml DMEM 1% BSA+25 mMHEPES were pipetted on top of the meshes and allowed to incubate at 37° C. for 35 min. The meshes were then transferred into a 6 well tissue culture plate and washed three times for 5 min each in 5 ml PBS. The meshes were fixed in 1 ml 3% paraformaldehyde+2% sucrose in PBS for 5 min at room temperature and the adherent cells stained with 0.5% crystal violet in 20% methanol for 15 min at room temperature. The meshes were washed extensively with water to remove nonspecific staining.

The results indicated that both the 804G-treated Mersilene™ and Vicryl™ meshes visibly stained darker than the control-treated meshes. Thus, the polyester and polyglactin 910 meshes supported 804G matrix adhesion and, more importantly, promoted rapid adhesion of epithelial cells to these materials. In contrast, no detectable cell staining was observed with the 804G-treated Prolene™ mesh which is consistent with the observation that polypropylene has a low capacity for binding proteins.

EXAMPLE 11

Growth of Epithelial Cells on 804G Matrix-Precoated Surgical Meshes

Mersilene™ and Vicryl™ meshes were precoated in 1 ml degassed 804G conditioned medium or degassed DMEM complete media containing 25 mMHEPES overnight at 4° C. Both mediums were degassed for 30 min at room temperature with a vane pump drawing a 23 mm Hg vacuum. The meshes were washed twice with sterile PBS and 1 ml RPMI complete medium containing $8\times10^4$ FGmet2 epithelial cells was pipetted on top of the meshes and allowed to incubate at 37° C.

After one day of growth, FGmet2 cells were visibly attached and spreading on 804G-treated meshes. The loose weave of the Mersilene™ mesh permitted better visualization of the cells than the tight weave of the Vicryl™ mesh. After two days the meshes were transferred to a new plate, fresh medium was added and the incubation was continued. After five days, cells were growing extensively along the Mersilene™ mesh fibers and appeared to cover more than 50% of the fiber surface. In contrast, cells growing on the control-treated mesh grew into a ball-shaped structure and did not exhibit significant growth along the fiber surface. These results demonstrate the unique ability of the soluble 804G matrix to adsorb onto medically important surfaces and promote the attachment and proliferation of cells on these materials.

EXAMPLE 12

Preservation of Corneal Explants with 804G Soluble Factor

Human donor corneal rims procured following penetrating keratoplasties were maintained in DMEM containing FCS (DMEM−) or in the same medium supplemented with soluble factors, including adhesion complex-associated matrix components, that are secreted in large amounts by 804G cells (DMEM+). After 72 hours, the tissue was processed for electron and immunofluorescence microscopy using various adhesion complex antibodies.

The epithelial layers became detached from the underlying stroma in corneal rims maintained in DMEM−. This detachment was correlated with a loss of adhesion complexes and their protein constituents. In contrast, after 72 hours in DMEM+, the epithelial layers appear healthy with numerous adhesion complexes in regions of cell-stromal attachment. In this wound model, no morphologic hemidesmosomes were observed in epithelial cells repopulating "wounds" in tissue material maintained in DMEM−. However, in DMEM+ media, morphologic hemidesmosomes were seen along the bare stroma in areas of epithelial cell-wound bed interaction.

It should be noted that the present invention is not limited to only those embodiments described in the Detailed Description. Any embodiment which retains the spirit of the present invention should be considered to be within its scope. However, the invention is only limited by the scope of the following claims.

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
(A) LENGTH: 295 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
(B) CLONE: 150 kD (xi) SEQUENCE DESCRIPTION: SEQ ID NO:1:

```
Glu Phe Glu Thr Leu Gln Glu Lys Ala Gln Val Asn Ser Arg Lys Ala
1               5                   10                  15

Gln Thr Leu Tyr Asn Asn Ile Asp Thr Thr Ile Gln Asn Ala Lys Glu
            20                  25                  30

Leu Asp Met Lys Ile Lys Asn Ile Leu Thr Asn Val His Ile Leu Leu
        35                  40                  45

Lys Gln Ile Ala Arg Pro Gly Gly Glu Gly Met Asp Leu Pro Val Gly
    50                  55                  60

Asp Trp Ser Arg Glu Ser Ala Glu Arg His Gly His Val Ala Glu Ser
65                  70                  75                  80

Arg Gly Arg Asp Phe Lys Lys His Leu Gln Glu Ala Glu Ala Gln Lys
                85                  90                  95

Met Glu Ala Gln Leu Leu Leu Asn Arg Ile Arg Thr Trp Leu Glu Ser
            100                 105                 110

His Gln Val Glu Asn Asn Gly Leu Leu Lys Asn Ile Arg Asp Ser Leu
        115                 120                 125

Asn Asp Tyr Glu Ala Lys Leu Gln Asp Leu Arg Ser Val Leu Gln Glu
    130                 135                 140

Ala Ala Ala Gln Gly Lys Gln Ala Thr Gly Leu Asn His Glu Asn Glu
145                 150                 155                 160

Gly Val Leu Gly Ala Ile Gln Arg Gln Met Lys Glu Met Asp Ser Leu
                165                 170                 175

Lys Lys Tyr Leu Thr Glu His Leu Ala Thr Ala Asp Ala Ser Leu Leu
            180                 185                 190
```

-continued

```
Gln Thr Asn Ser Leu Leu Gln Arg Met Asp Thr Ser Gln Lys Glu Tyr
        195                 200                 205

Glu Ala Trp Gln Ile Asp Ile Ser Leu Glu Gln His Pro Val His Asn
    210                 215                 220

Cys Leu Leu Arg Leu Thr Leu Arg Gln Asp Leu Ile Asp Leu Asn Phe
225                 230                 235                 240

Ser Phe Ser Val Pro Gln Val Val Asp Thr Arg Gln Leu Ala Ile Tyr
                245                 250                 255

Asn Arg His Ala Tyr Val Val Leu Gly Gly Ile Leu Val Ser Lys Val
            260                 265                 270

His Tyr Lys His Cys Pro Thr Cys Leu His Ser Leu Leu Ser Leu Val
        275                 280                 285

Phe Gly Gly Thr Lys Thr Tyr
    290                 295
```

(2) INFORMATION FOR SEQ ID NO:2:

(i) SEQUENCE CHARACTERISTICS:
(A) LENGTH: 360 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
(B) CLONE: laminin A (xi) SEQUENCE DESCRIPTION: SEQ ID NO:2:

```
Lys Phe Asp Thr Val Ser Glu Gln Lys Leu Gln Ala Glu Lys Asn Ile
1               5                   10                  15

Lys Asp Ala Gly Asn Phe Leu Ile Asn Gly Asp Leu Thr Leu Asn Gln
            20                  25                  30

Ile Asn Gln Lys Leu Asp Asn Leu Arg Asp Ala Leu Asn Glu Leu Asn
        35                  40                  45

Ser Phe Asn Lys Asn Val Asp Glu Glu Leu Pro Val Arg Glu Asp Gln
    50                  55                  60

His Lys Glu Ala Asp Ala Leu Thr Asp Gln Ala Glu Gln Lys Ala Ala
65                  70                  75                  80

Glu Leu Ala Ile Lys Ala Gln Asp Leu Ala Ala Gln Tyr Thr Asp Met
                85                  90                  95

Thr Ala Ser Ala Glu Pro Ala Ile Lys Ala Ala Thr Ala Tyr Ser Gly
            100                 105                 110

Ile Val Glu Ala Val Glu Ala Ala Gln Lys Leu Ser Gln Asp Ala Ile
        115                 120                 125

Ser Ala Ala Gly Asn Ala Thr Asp Lys Thr Asp Gly Ile Glu Glu Arg
    130                 135                 140

Ala His Leu Ala Asp Thr Gly Ser Thr Asp Leu Leu Gln Arg Ala Arg
145                 150                 155                 160

Gln Ser Leu Gln Lys Val Gln Asp Asp Leu Glu Pro Arg Leu Asn Ala
                165                 170                 175

Ser Ala Gly Lys Val Gln Lys Ile Ser Ala Val Asn Asn Ala Thr Glu
            180                 185                 190
```

-continued

```
His Gln Leu Lys Asp Ile Asn Lys Leu Ile Asp Gln Leu Pro Ala Glu
        195                 200                 205

Ser Gln Arg Asp Met Trp Lys Asn Ser Asn Ala Asn Ala Ser Asp Glu
    210                 215                 220

Ala Glu Ile Leu Lys Asn Val Leu Glu Ile Leu Glu Pro Val Ser Val
225                 230                 235                 240

Gln Thr Pro Lys Glu Leu Glu Lys Ala His Gly Ile Asn Arg Asp Leu
                245                 250                 255

Asp Leu Thr Asn Lys Asp Val Ser Gln Ala Asn Lys Gln Leu Asp Asp
            260                 265                 270

Val Glu Gly Ser Val Ser Lys Leu Asn Glu Leu Ala Glu Asp Ile Glu
        275                 280                 285

Glu Gln Gln His Arg Val Gly Ser Gln Ser Arg Gln Leu Gly Gln Glu
    290                 295                 300

Ile Glu Asn Leu Lys Ala Gln Val Glu Ala Ala Arg Gln Leu Ala Asn
305                 310                 315                 320

Ser Ile Lys Val Gly Val Asn Phe Lys Pro Ser Thr Ile Leu Glu Leu
                325                 330                 335

Lys Thr Pro Glu Lys Thr Lys Leu Leu Ala Thr Arg Thr Asn Leu Ser
            340                 345                 350

Thr Tyr Phe Arg Thr Thr Glu Pro
        355                 360
```

(2) INFORMATION FOR SEQ ID NO:3:

(i) SEQUENCE CHARACTERISTICS:
(A) LENGTH: 337 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
(B) CLONE: merosin (xi) SEQUENCE DESCRIPTION: SEQ ID NO:3:

```
Glu Leu Lys His Leu Leu Ser Pro Gln Arg Ala Pro Glu Arg Leu Ile
1               5                   10                  15

Gln Leu Ala Glu Gly Asn Leu Asn Thr Leu Val Thr Glu Met Asn Glu
            20                  25                  30

Leu Leu Thr Arg Ala Thr Lys Val Thr Ala Asp Gly Glu Gln Thr Gly
        35                  40                  45

Gln Asp Ala Glu Arg Thr Asn Thr Arg Ala Lys Ser Leu Gly Glu Phe
    50                  55                  60

Ile Lys Glu Leu Ala Arg Asp Ala Glu Ala Val Asn Glu Lys Ala Ile
65                  70                  75                  80

Lys Leu Asn Glu Thr Leu Gly Thr Arg Asp Glu Ala Phe Glu Arg Asn
                85                  90                  95

Leu Glu Gly Leu Gln Lys Glu Ile Asp Gln Met Ile Lys Glu Leu Arg
            100                 105                 110

Arg Lys Asn Leu Glu Thr Gln Lys Glu Ile Ala Glu Asp Glu Leu Val
        115                 120                 125
```

-continued

```
Ala Ala Glu Ala Leu Leu Lys Lys Val Lys Lys Leu Phe Gly Glu Ser
    130                 135                 140

Arg Gly Glu Asn Glu Glu Met Glu Lys Asp Leu Arg Glu Lys Leu Ala
145                 150                 155                 160

Asp Tyr Lys Asn Lys Val Asp Asp Ala Trp Asp Leu Leu Arg Glu Ala
                165                 170                 175

Thr Asp Lys Ile Arg Glu Ala Asn Arg Leu Phe Ala Val Asn Gln Lys
            180                 185                 190

Asn Met Thr Ala Leu Glu Lys Lys Lys Glu Ala Val Glu Ser Gly Lys
        195                 200                 205

Arg Gln Ile Glu Asn Thr Leu Lys Glu Gly Asn Asp Ile Leu Asp Glu
    210                 215                 220

Ala Asn Arg Leu Ala Asp Glu Ile Asn Ser Ile Ile Asp Tyr Val Glu
225                 230                 235                 240

Asp Ile Gln Thr Lys Leu Pro Pro Met Ser Glu Glu Leu Asn Asp Lys
                245                 250                 255

Ile Asp Asp Leu Ser Gln Glu Ile Lys Asp Arg Lys Leu Ala Glu Lys
            260                 265                 270

Val Ser Gln Ala Glu Ser His Ala Ala Gln Leu Asn Asp Ser Ser Ala
        275                 280                 285

Val Leu Asp Gly Ile Leu Asp Glu Ala Lys Asn Ile Ser Phe Asn Ala
    290                 295                 300

Thr Ala Ala Phe Lys Ala Tyr Ser Asn Ile Lys Asp Tyr Ile Asp Glu
305                 310                 315                 320

Ala Glu Lys Val Ala Lys Glu Ala Lys Asp Leu Ala His Glu Ala Thr
                325                 330                 335

Lys
```

What is claimed is:

1. An article of manufacture comprising a trans-epithelial appliance coated with a soluble hemidesmosome formation-inducing factor obtainable from 804G or NBT-II rat bladder carcinoma cells, wherein the factor induces epithelial cell attachment-to the coated trans-epithelial appliance.

2. The article of claim 1, wherein said appliance is a shaped article selected from the group consisting of indwelling catheter, needle, metal pin, metal rod, colostomy tube, dental abutment piece and surgical mesh.

3. The article of claim 1, further comprising epithelial cells deposited on said hemidesmosome formation-inducing composition.

4. The article of claim 1, wherein said appliance is used in vivo.

5. The article of claim 1, wherein said appliance is made of or coated with a biocompatible metal.

6. The article of claim 5, wherein said metal is stainless steel or titanium.

7. The article of claim 1, wherein said appliance is made of or coated with a ceramic material.

8. The article of claim 7, wherein said material is hydroxyapatite.

9. The article of claim 1, wherein said appliance is made of or coated with a polymer.

10. The article of claim 9, wherein said polymer is selected from the group consisting of polyester, polyglycolic acid and a polygalactose-polyglycolic acid copolymer.

11. A method for inducing epithelial cell attachment to a trans-epithelial [appliance] *surface,* comprising the following steps:

(a) coating a trans-epithelial [appliance] *surface* with a soluble hemidesmosome formation-inducing factor obtainable from 804G or NBT-II rat bladder carcinoma cells, and (b) incubating the coated trans-epithelial [appliance] *surface* with epithelial cells under conditions necessary to induce epithelial cell attachment to the coated trans-epithelial [appiance] *surface*.

12. The method of claim 11, wherein said [appliance] *surface* is selected from the group consisting of *the surface of an* indwelling catheter, *a* needle, *a* metal pin, *a* metal rod, *a* colostomy tube, *a* dental abutment piece and *a* surgical mesh.

13. The method of claim 11, wherein said [appliance] *surface* is made of or coated with a polymer.

14. The method of claim 13, wherein said polymer is selected from the group consisting of polyester, polyglycolic acid and a polygalactose-polyglycolic acid copolymer.

*15. The method of claim 11, wherein said surface is the surface of a tooth.*

*16. The method of claim 15, wherein said tooth is in an area affected with periodontitis or gingivitis and said soluble factor promotes adhesion of periodontal tissue to said tooth.*

*17. The method of claim 16, wherein said soluble factor is produced by recombinant means.*

*18. The method of claim 16, wherein said periodontal tissue is gingival tissue or gum junctional epithelium.*

* * * * *